(12) United States Patent
Henton et al.

(10) Patent No.: US 7,135,571 B2
(45) Date of Patent: *Nov. 14, 2006

(54) PROCESSES FOR PREPARING ANHYDROUS AND HYDRATE FORMS OF ANTIHISTAMINIC PIPERIDINE DERIVATIVES, POLYMORPHS AND PSEUDOMORPHS THEREOF

(75) Inventors: Daniel R Henton, Midland, MI (US); Frederick J McCarty, Cincinnati, OH (US); Susan I Tripp, Lee's Summit, MO (US); Jill E DeWitt, Kansas City, MO (US)

(73) Assignee: Aventis Pharmaceuticals, Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/160,883

(22) Filed: Jun. 3, 2002

(65) Prior Publication Data

US 2002/0193601 A1    Dec. 19, 2002

Related U.S. Application Data

(60) Continuation of application No. 09/803,476, filed on Mar. 9, 2001, now abandoned, which is a continuation of application No. 09/213,161, filed on Dec. 17, 1998, now abandoned, which is a continuation of application No. 08/815,641, filed on Mar. 13, 1997, now abandoned, which is a continuation of application No. 08/439,673, filed on May 12, 1995, now abandoned, which is a division of application No. 08/417,161, filed on Apr. 11, 1995, now abandoned, which is a continuation-in-part of application No. 08/245,731, filed on May 18, 1994, now abandoned.

(51) Int. Cl.
    *C07D 211/22* (2006.01)
(52) U.S. Cl. .......................... 546/239; 514/317
(58) Field of Classification Search ................ 546/239, 546/240; 514/317
    See application file for complete search history.

(56) References Cited

U.S. PATENT DOCUMENTS

| | | | |
|---|---|---|---|
| 5,204,249 A | | 4/1993 | Schwartz |
| 5,375,693 A | | 12/1994 | Woosley |
| 5,574,045 A | * | 11/1996 | Ortyl et al. ............ 514/317 |
| 5,578,610 A | | 11/1996 | D'Ambra |
| 5,631,375 A | | 5/1997 | King |
| 5,738,872 A | * | 4/1998 | Ortyl et al. ............ 424/452 |
| 5,855,912 A | | 1/1999 | Ortyl et al. |
| 5,932,247 A | | 8/1999 | Ortyl et al. |
| 6,037,353 A | | 3/2000 | Woodward et al. |
| 6,039,974 A | * | 3/2000 | MacLaren et al. ....... 424/472 |
| 6,113,942 A | | 9/2000 | Ortyl et al. |
| 6,147,216 A | | 11/2000 | Krauss |
| 6,187,791 B1 | | 2/2001 | Woodward et al. |
| 6,242,606 B1 | | 6/2001 | Krauss |
| 6,399,632 B1 | | 6/2002 | Woodward et al. |
| 6,613,906 B1 | | 9/2003 | Davies et al. |

FOREIGN PATENT DOCUMENTS

| | | |
|---|---|---|
| CA | 1123438 | 5/1982 |
| CA | 1123439 | 5/1982 |
| CA | 2117892 | 10/1993 |
| CA | 2181089 | 12/1994 |
| IL | 117237 | 1/2001 |

(Continued)

OTHER PUBLICATIONS

Bennett et al. "Concise chemical and technical dictionary" Chem. Pub. p. 553 (1976).*

(Continued)

*Primary Examiner*—Celia Chang
(74) *Attorney, Agent, or Firm*—Finnegan, Henderson, Farabow, Garrett & Dunner, LLP

(57) ABSTRACT

The present invention is related to novel processes for preparing anhydrous and hydrated forms of piperidine derivatives, polymorphs and pseudomorphs thereof of the formulas

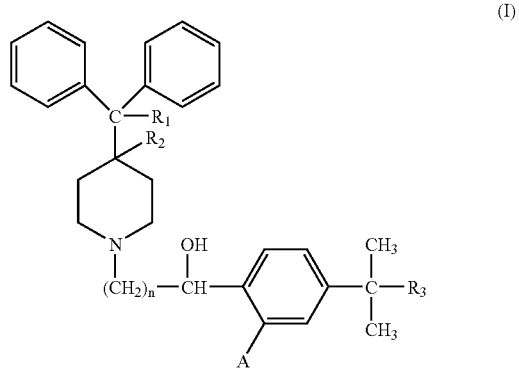

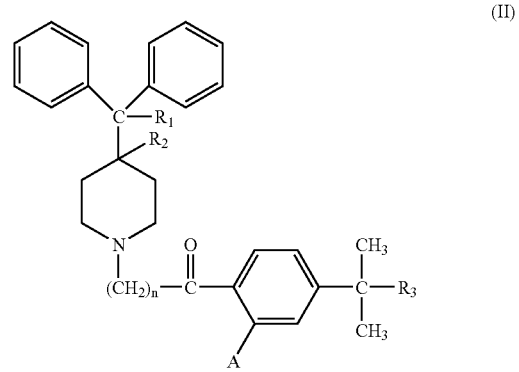

which are useful as antihistamines, antiallergic agents and bronchodilators.

1 Claim, No Drawings

FOREIGN PATENT DOCUMENTS

| IL | 134917 | 7/2001 |
|---|---|---|
| IL | 134771 | 2/2002 |
| WO | WO 94/03170 | 2/1994 |
| WO | WO 94/09008 | 4/1994 |
| WO | WO 95/00480 | 1/1995 |
| WO | WO 96/26726 | 9/1996 |

OTHER PUBLICATIONS

Evans et al. "An introduction to crystal chemistry" Cambridge p. 266-298, 396 (1964).*
See copies in parent cases.*
Rouli "The right stuff" Chem. Eng. News Feb. 24, p. 32-35 (2003).*
Cheronis "semimicro experimental organic chemistry" De Graff p. 8, (1958).*
Salole et al. "Effect of solvent deposition on . . . " Derwent Acc. No. 86-22527 (1985).*
Jalonen et al. "The crystal growth of carbamazepine . . . " Derwent Acc. No. 90-02014 (1989).*
Foks et al. "Effect of temperature and supersaturation . . . " SciSearch 02857044 (1993).*
Terao et al. "Second order nonliner . . . " Pascal No. 92-0591460 (1990).*
Internet page printout of Hawley's Condensed Chemical Dictionary 1 (14th ed. 2002) (definitions of amorphous and conformation).
Chan, K.Y. et al.; Direct Enantiomerica Separation of Terfenadine and Its Major Acid Metabolite by High-Performance Liquid Chromatography, and the Lack of Stereoselective Terfenadine Enantiomer Biotransformation in Man; CA 116:50726 (1992).
Henton, D. et al; Process for Preparing Anhydrous and Hydrate of Antihistaminic Piperidine Derivatives (Polymorphs and Pseudomorphs); CA-124:202030 (1996).
Morrison, R.T. & Boyd, R.N.; Organic Chemistry 75 (1973).
Office Action dated May 26, 2004, in copending U.S. Appl. No. 10/162,011.
Office Action dated May 4, 2004, in copending U.S. Appl. No. 10/214,262.
Office Action dated Oct. 22, 2004, in copending U.S. Appl. No. 10/386,812.
Office Action dated May 17, 2004, in copending U.S. Appl. No. 10/125,094.
Office Action dated Apr. 18, 2003 in copending U.S. Appl. No. 10/125,094.
Eagleson, M.; Concise Encyclopedia Chemistry 872-873 (1944).
Cheronis, N.D.; Semimicro Experimental Organic Chemistry, A Laboratory Manual 16-17 (J de Gratt 1958).
English-Language Translation of Sep. 21, 2005, Letter from Seligsohn Gabrielli Levit & Co. to Israeli Registrar of Patents.
English-Language Translation of Nov. 1, 2005, Letter from Israeli Patent Office to Seligsohn Gabrielli Levit & Co.
English-Language Translation of Statement of Claim, C.F. 1088/06 (Israel Patent No. 134,917).
English-Language Translation of Urgent Application For Interlocutory Remedies, C.F. 1088/06 (Israel Patent No. 134,917).
English-Language Translation of Statement of Claim, C.F. 1152/05 (Israel Patent Nos. 117,237 and 134,771).
English-Language Translation of Urgent Application For Interlocutory Remedies, C.F. 1152/05 (Israel Patent Nos. 117,237 and 134,771).
Declaration of Prof. Joel Bernstein.
Declaration David E. Bugay, Ph.D.
English-Language Translation of Respondent's Reply to Application for Grant of Interlocutory Remedies, C.F. 1088/06.
Expert Opinion of Prof. Anthony Michael Glazer.
Report and Declaration of Peter W. Stephens.
Report and Declaration of Dr. Clare Grey.
Report and Declaration of Marc D. Hollingsworth, Ph.D.
English-Language Translation of Affidavit of Prof. Abraham Rubinstein.
English-Language Translation of Affidavit of Dr. Shmuel Cohen.
English-Language Translation of Affidavit of Mike Netz.
English-Language Translation of Affidavit of Netanel Aharonov.
English-Language Translation of Affidavit of Hagit Saban.
Letter from Thomas Irving to Liad Whatstein regarding Motion No. 2731/06 in C.F. 1088/06, dated Mar. 29, 2006.
Declaration of David E. Bugay, Ph.D., dated Apr. 2, 2006, and Exhibits A-E.
Declaration of Prof. Joel Bernstein, dated Apr. 2, 2006.
Urgent Application For Interlocutory Remedies, C.F. 1088/06 (Israel Patent No. 134,917).
Statement of Claim, C.F. 1088/06 (Israel Patent No. 134,917).
Statement of Reply, C.F. 1088/06 (Israel Patent No. 134,917) and English-language translation.
Respondent's Reply to Application for Grant of Interlocutory Remedies and English-language translation.
Applicant's Reply to Respondent's Response to the Application for Interlocutory Remedies, C.F. 1088/06 (Israel Patent No. 134,917) and English-language translation.
Ulicky, L. et al.; Comprehensive Dictionary of Physical Chemistry 21 (Prentice Hall 1992).
Dean, J.A.; Analytical Chemistry Handbook 10.24 (McGraw Hill 1995).
European Search Report in European Application No. 01124314.4-2101, dated Dec. 20, 2001.
PCT International Search Report in Application No. PCT/US95/04942, dated Aug. 10, 1995.
Canadian Office Action in Application No. 2,189,007, dated Nov. 6, 1998.
Argentine Search Report in Application No. 332047, dated Sep. 13, 1999.
Norwegian Search Report in Application No. 1996 4859, dated Nov. 21, 2001.
Office Action dated Jun. 26, 2003, in co-pending U.S. Appl. No. 10/162,011.
Office Action dated Apr. 18, 2003, in co-pending U.S. Appl. No. 10/125,094.
Office Action dated Aug. 8, 2003, in co-pending U.S. Appl. No. 10/214,262.
Amon, U. et al.; Anti-allergic effects of H1-receptor antagonists on histamin-containing cells; 178(8) Dermatologische Monatsschrift 327-33 (1992).
Bailey, D.G. et al.; Effect of Grapefruit Juice and Naringin on Nisoldipine Pharmacokinetics; 54(6) Clinical Pharmacology & Therapeutics 589-94 (1993).
Bailey, D.G. et al.; Grapefruit Juice—Felodipine Interaction: Mechanism, Predictability, and Effect of Naringin; 53 Clinical Pharmacology & Therapeutics 637-42 (1993).
Bailey, D.G. et al.; Grapefruit Juice and Drugs: How Significant is the Interaction; 26(2) Clinical Pharmacokinetics 91-98 (1994).
Bailey, D.G. et al.; Grapefruit Juice—Felodipine Interaction: Reproducibility and Characterization with the Extended Release Drug Formulation; 40 Br. J. Clinical Pharmacology 135-40 (1995).
Baroody, F. et al.; The Effects of $H_1$ antihistamines on the Early Allergic Response; 63 Annals of Allergy 551-55 (1989).
Cantilena, L. et al.; Effect of Cimetidine and Ranitidine on the Pharmacokinetics and ECG Pharmacodynamics of Terfenadine; 53(2) Clinical Pharmacology & Therapeutics 161 (1993).
Charlesworth, E.N. et al.; Cutaneous Late-Phase Response in Food-Allergic Children and Adolescents with Atopic Dermatitis; 23 Clinical and Experimental Allergy 391-98 (1993).
Crumb, W.J. et al.; Blockade of Multiple Human Cardiac Potassium Currents by the Antihistamine Terfenadine: Possible Mechanism for Terfenadine-Associated Cardiotoxicity; 47 Molecular Pharmacology 181-90 (1995).
Gupta, S.K. et al.; High-Performance Liquid Chromatographic Determination of Terfenadine in Commercial Tablets; 361 J. Chromatography 403-06 (1986).
Honig, P.K. et al.; Changes in the Pharmacokinetics and Electrocardiographic Pharmacodynamics of Terfenadine with Concomitant Administration of Erythromycin; 52(3) Clinical Pharmacology & Therapeutics 231-38 (1992).

Honig, P.K. et al.; Effect of Concomitant Administration of Cimetidine and Ranitidine on the Pharmacokinetics and Electrocardiographic Effects of Terfenadine; 45(1) Eur. J. Clinical Pharmacology 41-46 (1993).

Honig, P.K. et al.; Itraconazole Affects Single-Dose Terfenadine Pharmacokinetics and Cardiac Repolarization Pharmacodynamics; 33(12) J. Clinical Pharmacology 1201-06 (1993).

Honig, P.K. et al.; The Effect of Fluconazole on the Steady-State Pharmacokinetics and Electrocardiographic Pharmacodynamics of Terfenadine in Humans; 53(6) Clinical Pharmacology & Therapeutics 630-36 (1993).

Honig, P.K. et al.; Terfenadine-Ketoconazole Interaction: Pharmacokinetic and Electrocardiographic Consequences; 269(12) J. Am. Med. Assoc. 1513-18 (1993).

Honig, P.K. et al.; Comparison of the Effect of the Macrolide Antibiotics Erythromycin, Clarithromycin and Azithromycin on Terfenadine Steady-State Pharmacokinetics and Electrocardiographic Parameters; 7(3) Drug Invest. 148-56 (1994).

Honig, P.K. et al.; Population Variability in the Pharmacokinetics of Terfenadine: the Case for a Pseudo-Polymorphism with Clinical Implications; 11(2) Drug Metabolism and Drug Interactions 161-68 (1994).

Humphreys, F. & Shuster, S.; The Effect of Nedocromil on Weal Reactions in Human Skin; 24 Br. J. Clinical Pharmacology 405-08 (1987).

Jurima-Romet, M. et al.; Terfenadine Metabolism in Human Liver: In Vitro Inhibition by Macrolide Antibiotics and Azole Antifungals; 22(6) Drug Metabolism and Disposition 849-57 (1994).

Jurima-Romet, M. et al.; Induction of CYP3A and Associated Terfenadine N-Dealkylation in Rat Hepatocytes Cocultured with 3T3 Cells; 11 Cell Biology and Toxicology 313-27 (1995).

Kietzmann, H. et al.; Comparison of Cetirizine and Terfenadine in the Treatment of Chronic Idiopathic Urticaria; 65 Annals of Allergy 498-500 (1990).

Krause, L.B. & Shuster, S.; The Effect of Terfenadine on Dermographic Wealing; 110 Br. J. Dermatology 73-79 (1984).

Lipicky, R.J.; A Viewpoint on Drugs that Prolong that $QT_c$ Interval; 72 Am. J. Cardiology 53B-59B (1993).

Massey, W.A. & Lichtenstein, L.M.; The Effects of Antihistamines Beyond $H_1$ Antagonism in Allergic Inflammation; 86 J. Allergy and Clinical Immunology 1019-24 (1990).

Massey, W.A. et al.; Cutaneous IgE-Mediated Inflammatory Lesion Size is Inhibited by an $H_1$ Antagonist (Terfenadine) while Mediator Release is Unaffected In Vivo and In Vitro; 23 Clinical and Experimental Allergy 399-405 (1993).

Mathews, D.R. et al.; Torsades de Pointes Occurring in Association with Terfenadine Use (Letter and Reply); 266(17) J. Am. Med. Assoc. 2375-76 (1991).

Monahan, B.P. et al.; Torsades de Pointes Occurring in Association with Terfenadine Use; 264(21) J. Am. Med. Assoc. 2788-90 (1990).

Naclerio, R.M. et al.; Terfenadine, an $H_1$ Antihistamine, Inhibits Histamine Release In Vivo in the Human; 142(1) Am. Rev. Respir. Dis. 167-171 (1990).

Ramachers, U. et al.; Direct Effects of Second-Generation $H_1$-Receptor Antagonists on the Activation of Human Basophils; 41 Agent Actions Special Conference Issue C45-46 (1994).

Rampe, D. et al.; Effects of Terfenadine and Its Metabolites on a Delayed Rectifier $K^+$ Channel Cloned from Human Heart; 44(6) Molecular Pharmacology 1240-45 (1993).

Rau, S.E. et al; Inhibition of Terfenadine Metabolism by Coadministration of Grapefruit Juice in Humans (Abstract); Clin. Invest. Med. B16 (1995).

Shuster, S.; Comparative Trial of Two Non-Sedative $H_1$ Antihistamines, Terfenadine and Astemizole, for Hay Fever; 41 Thorax 654-56 (1986) (Abstract).

Shuster, S.; Antihistamines in the Treatment of Urticarial Disorders; 42(4A) Cutis 26-28 (1988).

Terhechte, A. & Blascke, G.; Indirect and Direct Racemate Separation of Terfenadine and its Main Metabolite MDL 16,455A (Translation); 324 Arch. Pharm. 710 (1991).

Terhechte, A. & Blascke, G.; Studies of the Enantiomers of the Metabolite Terfenadine: Designation of the Main Metabolite Derived from Serum and Urine through HPLC and Solid Phase Extraction; Internationales Chiralitatssymposium (1992).

Terhechte, A. & Blascke, G.; Investigation of the Stereoselective Metabolism of the Chiral $H_1$-Antihistaminic Drug Terfenadine by High-Performance Liquid Chromatography; 694 J. Chromatography A 219-25 (1995).

Togias, A.G. et al; In Vivo and In Vitro Effects of Antihistamines on Mast Cell Mediator Release: a Potentially Important Property in the Treatment of Allergic Disease; 63 Annals of Allergy 465-69 (1989).

van Bavel, J. et al.; Intranasal Fluticasone Proprionate is More Effective than Terfenadine Tablets for Seasonal Allergic Rhinitis; 154 Arch. Internal Medicine 2699-2704 (1994).

Wagenmann, M. et al.; The Effect of Terfenadine on Unilateral Nasal Challenge with Allergen; 93(3) J. Allergy and Clinical Immunology 594-605 (1994).

Yang, T. et al.; Block of a Human Cardiac $K^+$ Channel by Terfenadine and its Enantiomers, but not by Terfenadine Carboxylate (Abstract); 17 Pacing Clinical Electrophysiology 777 (1994).

Yang, T. et al; Mechanism of Block of A Human Cardiac Potassium Channel by Terfenadine Racemate and Enantiomers; 115 Br. J. Pharmacology 267-74 (1995).

Yun, C. et al.; Oxidation of the Antihistaminic Drug Terfenadine in the Human Liver Microsomes; 21(3) Drug Metabolism and Disposition 403-09 (1993).

Zamani, K. et al.; Enantiomeric Analysis of Terfenadine in Rat Plasma by HPLC; 3 Chirality 467-70 (1991).

McCauley, J.A. et al.; The Effect of Polymorphism and Metastability on the Characterization and Isolation of Two Pharmaceutical Compounds; 26 J. Phys. D.: Appl. Phys. 85-89 (1993).

Kawai, S.H. et al.; A Facile Synthesis of an Oxidation Product of Terfenadine; 59(10) J. Organic Chemistry 2620-22 (1994).

Surapaneni, S. & Khalil, S.K.W.; A Preliminary Pharmacokinetic Study of the Enantiomers of the Terfenadine Acid Metabolite in Humans; 6 Chirality 479-483 (1994).

Surapaneni, S. & Khalil, S.K.W.; A Sensitive HPLC Method for the Determination of Terfenadine and its Metabolite in Human Plasma; 17(11) J. Liquid Chromatography 2419-28 (1994).

Chan, K.Y. et al.; Direct Enantiomeric Separation of Terfenadine and its Major Acid Metabolite by High-Performance Liquid Chromatography, and the Lack of Stereoselective Terfenadine Enantiomer Biotransformation in Man; 571 J. Chromatography 291-97 (1991).

Chen, T.-M. et al.; Determination of the Metabolites of Terfenadine in Human Urine by Thermospray Liquid Chromatography—Mass Spectrometry; 9(10-12) J. Pharmaceutical and Biomedical Analysis 929-33 (1991).

Coutant, J.E. et al.; Determination of Terfenadine and Terfenadine Acid Metabolite in Plasma Using Solid-Phase Extraction and High-Performance Liquid Chromatography with Flourescence Detection; 570 J. Chromatography 139-48 (1991).

Garteiz, D.A. et al.; Pharmacokinetics and Biotransformation Studies of Terfenadine in Man; 32 Drug Research 1185-90 (1982).

Gramberg, L.G. et al.; Pilot Study on the Determination of Terfenadine in Human Plasma by GC/MS; A87431 Rapp Tno Hoofdgroep Voeding Voedingsmiddelen Tno 2-12 (1987).

Maurer, H. & Pfleger K.; Identification and Differentiation of Alkylamine Antihistamines and their Metabolites in Urine by Computerized Gas Chromatography-Mass Spectrometry; 430(1) J. Chromatography 31-41 (1988).

Okerholm, R.A. et al.; Bioavailability of Terfenadine in Man; 2 Biopharmaceutics & Drug Disposition 185-90 (1981).

Rao, N. et al.; Pharmacokinetics of Terfenadine-Acid-Metabolite, MDL 16,455, in Healthy Geriatric Subjects (Abstract); 12 Pharm. Research S-386 (1995).

Russell, T. et al.; A Comparison of MDL 16,455A Pharmacokinetics by Gender (Abstract); 12 Pharm. Research S-389 (1995).

Woodward, J.K. & Munro, N.L.; Terfenadine, the First Non-Sedating Antihistamine; 32 Drug Research 1154-56 (1982).

Opponent's Statement of Case filed in pending Israeli Opposition proceeding IL 113747.

Opponent's Statement of Case filed in pending Israeli Opposition proceeding IL 134917.

Office Action dated Feb. 18, 2004, in copending U.S. Appl. No. 10/386,812.

Rouhi et al.; The Right Stuff, Chemical and Engineering News 32-35 (Feb. 24, 2003).

Physical Properties of Liquids, Encyclopedia Britannica Online (2004).

Distinction between Crystalline and Amorphous Solids, Encyclopedia Britannica Online (2004).

Third Party Observation submitted in European Patent Application No. 01124314.4 on Aug. 14, 2006.

Declaration of Dr. Marcus F. Brackeen, signed Jul. 7, 2006, and submitted in Israeli litigation docket No. C.F. 1088/0, with exhibits A-F.

Declaration of Prof. Anthony Michael Glazer, signed Jul. 7, 2006, and submitted in Israeli litigation docket No. C.F. 1088/06, with exhibit 1.

Declaration of Prof. Clare Grey, signed Jul. 7, 2006, and submitted in Israeli litigation docket No. C.F. 1088/06, with exhibits A-F.

Declaration of Dr. Mark D. Hollingsworth, signed Jul. 6, 2006, and submitted in Israeli litigation docket No. C.F. 1088/06, with exhibits A-E.

Declaration of Dr. Alan P. Kozikowsky, signed Jul. 7, 2006, and submitted in Israeli litigation docket no. C.F. 1088/06, with exhibits A-M.

Declaration of Dr. William E. Mayo, signed Jul. 7, 2006, and submitted in Israeli litigation docket No. C.F. 1088/0, with exhibits A-M.

Declaration of Prof. Abraham Rubinstein, signed Jul. 9, 2006, and submitted in Israeli litigation docket No. C.F. 1088/06, with exhibits A-C, Including English-language Translation of Appendix B.

Declaration of Prof. Peter W. Stephens, signed Jul. 7, 2006, and submitted in Israeli litigation docket No. C.F. 1088/06.

Affidavit of Lilach Goldman, dated Jul. 10, 2006.

English-language Translation of Affidavit of Lilach Goldman, dated Jul. 10, 2006.

* cited by examiner

PROCESSES FOR PREPARING ANHYDROUS AND HYDRATE FORMS OF ANTIHISTAMINIC PIPERIDINE DERIVATIVES, POLYMORPHS AND PSEUDOMORPHS THEREOF

This is a continuation of application Ser. No. 09/803,476, filed Mar. 9, 2001 now abandoned, which is a continuation of application Ser. No. 09/213,161, filed Dec. 17, 1998, now abandoned, which is a continuation of application Ser. No. 08/815,641 filed Mar. 13, 1997, now abandoned, which is a continuation of application Ser. No. 08/439,673, filed May 12, 1995, now abandoned, which is divisional of Ser. No. 08/417,161, filed Apr. 11, 1995, now abandoned, which is a continuation-in-part of Ser. No. 08/245,731, filed May 18, 1994, now abandoned.

The present invention is related to novel processes for preparing anhydrous and hydrated forms of piperidine derivatives, polymorphs and pseudomorphs thereof which are useful as antihistamines, antiallergic agents and bronchodilators [U.S. Pat. No. 4,254,129, Mar. 3, 1981, U.S. Pat. No. 4,254,130, Mar. 3, 1981 and U.S. Pat. No. 4,285,958, Apr. 25, 1981].

SUMMARY OF THE INVENTION

The present invention provides a process for preparing anhydrous, pharmaceutically acceptable acid addition salts of piperidine derivatives of the formulas

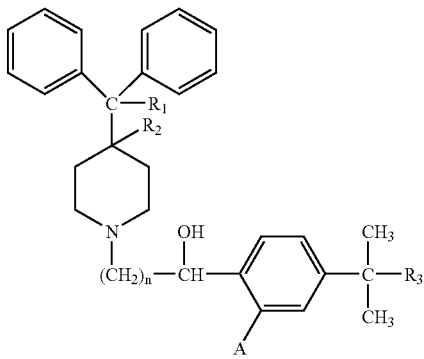

(I)

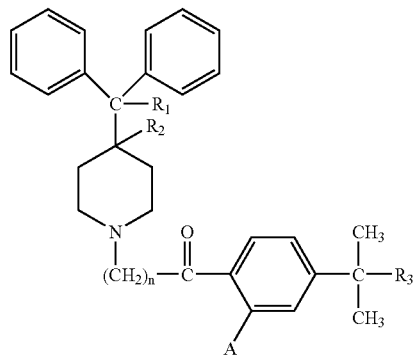

(II)

wherein
  $R_1$ represents hydrogen or hydroxy;
  $R_2$ represents hydrogen; or
  $R_1$ and $R_2$ taken together form a second bond between the carbon atoms bearing $R_1$ and $R_2$;
  n is an integer of from 1 to 5;
  $R_3$ is —$CH_2OH$, —COOH or —COOalkyl wherein the alkyl moiety has from 1 to 6 carbon atoms and is straight or branched;
  each of A is hydrogen or hydroxy; and
  pharmaceutically acceptable salts and individual optical isomers thereof, comprising subjecting the corresponding hydrated, pharmaceutically acceptable acid addition salt to an azeotropic distillation.

In addition, the present invention also provides a process for preparing anhydrous, pharmaceutically acceptable acid addition salts of piperidine derivatives of the formula

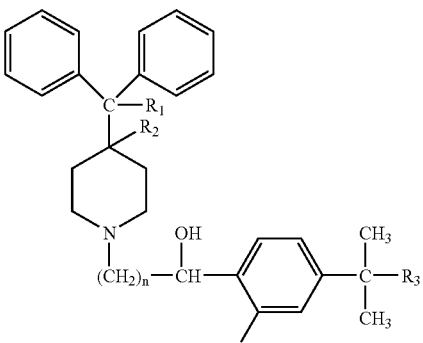

(I)

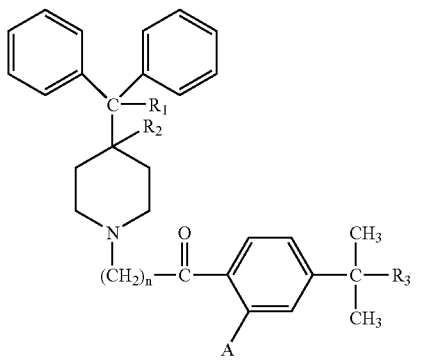

(II)

wherein
  $R_1$ represents hydrogen or hydroxy;
  $R_2$ represents hydrogen; or
  $R_1$ and $R_2$ taken together form a second bond between the carbon atoms bearing $R_1$ and $R_2$;
  n is an integer of from 1 to 5;
  $R_3$ is —$CH_2OH$, —COOH or —COOalkyl wherein the alkyl moiety has from 1 to 6 carbon atoms and is straight or branched;
  each of A is hydrogen or hydroxy; and
  pharmaceutically acceptable salts and individual optical isomers thereof, comprising subjecting the corresponding hydrated, pharmaceutically acceptable acid addition salt to a water-minimizing recrystallization.

In addition, the present invention provides a process for preparing the hydrated, pharmaceutically acceptable acid addition salts of piperidine derivatives of the formula

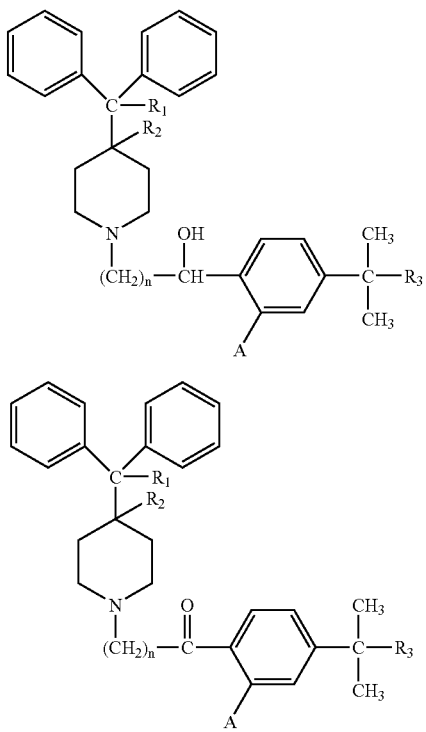

wherein
- $R_1$ represents hydrogen or hydroxy;
- $R_2$ represents hydrogen; or
- $R_1$ and $R_2$ taken together form a second bond between the carbon atoms bearing $R_1$ and $R_2$;
- n is an integer of from 1 to 5;
- $R_3$ is —$CH_2OH$, —COOH or —COOalkyl wherein the alkyl moiety has from 1 to 6 carbon atoms and is straight or branched;
- each of A is hydrogen or hydroxy; and
- pharmaceutically acceptable salts and individual optical isomers thereof, comprising subjecting the corresponding anhydrous, pharmaceutically acceptable acid addition salts to an aqueous recrystallization.

In addition, the present invention provides processes for preparing polymorphs of anhydrous 4-[4-[4-(Hydroxydiphenylmethyl)-1-piperidinyl]-1-hydroxybutyl]-α,α-dimethylbenzeneacetic acid hydrochloride designated herein as Form I and Form III and processes for preparing psuedomorphs of hydrated 4-[4-[4-(Hydroxydiphenylmethyl)-1-piperidinyl]-1-hydroxybutyl]-α,α-dimethylbenzeneacetic acid hydrochloride designated herein as Form II and Form IV.

The Form I polymorph may be identified by the following characteristics: a visual melting point (capillary tube) in the range of about 196–201° C.; a melt endotherm with extrapolated onset in the range of about 195–199° C. as determined by differential scanning calorimetry; and an X-ray powder diffraction pattern essentially as shown in Table 1 wherein the XRPD patterns were measured using a powder diffractometer equipped with a Co X-ray tube source. The sample was illuminated with Co $K\alpha_1$ radiation and XRPD data were collected from 5 to 55° 2Θ. (intensities may vary radically due to preferred orientation).

TABLE 1

| D-Space, Angstroms | Intensity, $I/I_o$, % |
|---|---|
| 11.8 | 30 |
| 7.3 | 30 |
| 6.3 | 65 |
| 5.9 | 35 |
| 5.0 | 45 |
| 4.8 | 100 |
| 4.4 | 45 |
| 3.9 | 60 |
| 3.8 | 75 |
| 3.7 | 30 |

The Form III polymorph may be identified by the following characteristics: a visual melting point (capillary tube) in the range of about 166–171° C.; a broad endotherm below about 90° C., a melt endotherm with an extrapolated onset of about 166° C. as determined by differential scanning calorimetry; and an X-ray powder diffraction pattern essentially as shown in Table 2 wherein the XRPD patterns were measured using a powder diffractometer equipped with a Co X-ray tube source. The sample was illuminated with Co $K\alpha_1$ radiation and XRPD data were collected from 5 to 55° 2Θ. (intensities may vary radically due to preferred orientation).

TABLE 2

| D-Space, Angstroms | Intensity, $I/I_o$, % |
|---|---|
| 9.0 | 95 |
| 4.9 | 100 |
| 4.8 | 35 |
| 4.6 | 25 |
| 4.5 | 25 |
| 3.7 | 25 |

The Form II pseudomorph may be identified by the following characteristics: a visual melting point (capillary tube) in the range of about 100–105° C.; a large broad endotherm below about 100° C. and a small endothermic peak (about 2 joules/gram) with extrapolated onsets in the range of about 124–126° C. as determined by differential scanning calorimetry; and an X-ray powder diffraction pattern essentially as shown in Table 3 wherein the XRPD patterns were measured using a powder diffractometer equipped with a Co X-ray tube source. The sample was illuminated with Co $K\alpha_1$ radiation and XRPD data were collected from 5 to 55° 2Θ. (intensities may vary radically due to preferred orientation).

TABLE 3

| D-Space, Angstroms | Intensity, $I/I_o$, % |
|---|---|
| 7.8 | 45 |
| 6.4 | 44 |
| 5.2 | 85 |
| 4.9 | 60 |
| 4.7 | 80 |
| 4.4 | 55 |
| 4.2 | 50 |
| 4.1 | 60 |
| 3.7 | 75 |
| 3.6 | 60 |
| 3.5 | 50 |

The Form IV pseudomorph may be identified by the following characteristics: a visual melting point (capillary tube) in the range of about 113–118° C.; two broad overlapping endotherms below about 100° C. and an additional endotherm with an extrapolated onset at approximately 146° C. as determined by differential scanning calorimetry and an X-ray powder diffraction pattern essentially as shown in Table 4 wherein the XRPD patterns were measured using a powder diffractometer equipped with a Co X-ray tube source. The sample was illuminated with Co $K\alpha_1$ radiation and XRPD data were collected from 5 to 55° 2Θ. (intensities may vary radically due to preferred orientation).

TABLE 4

| D-Space, Angstroms | Intensity, $I/I_o$, % |
|---|---|
| 10.4 | 60 |
| 7.0 | 45 |
| 6.4 | 50 |
| 5.3 | 100 |
| 5.2 | 55 |
| 4.3 | 75 |
| 4.1 | 50 |
| 4.0 | 45 |
| 3.8 | 60 |
| 3.5 | 55 |

DETAILED DESCRIPTION OF THE INVENTION

Pharmaceutically acceptable acid addition salts of the compounds of formula (I) and (II), both anhydrous and hydrated, are those of any suitable inorganic or organic acid. Suitable inorganic acids are, for example, hydrochloric, hydrobromic, sulfuric, and phosphoric acids. Suitable organic acids include carboxylic acids, such as, acetic, propionic, glycolic, lactic, pyruvic, malonic, succinic, fumaric, malic, tartaric, citric, cyclamic, ascorbic, maleic, hydroxymaleic, and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, and mandelic acid, sulfonic acids, such as, methanesulfonic, ethanesulfonic and β-hydroxyethanesulfonic acid.

As used herein, the term "hydrate" refers to a combination of water with a compound of formula (I) or (II) wherein the water retains its molecular state as water and is either absorbed, adsorbed or contained within a crystal lattice of the substrate molecule of formula (I) or (II).

As used herein, the term "adsorped" refers to the physical state wherein the water molecule in the hydrated, pharmaceutically acceptable acid addition salts of piperidine derivatives of the formula (I) and (II) is distributed over the surface of the solid hydrated, pharmaceutically acceptable acid addition salts of piperidine derivatives of the formula (I) and (II).

As used herein, the term "absorbed" refers to the physical state wherein the water molecule in the hydrated, pharmaceutically acceptable acid addition salts of piperidine derivatives of the formula (I) and (II) is distributed throughout the body of the solid hydrated, pharmaceutically acceptable acid addition salts of piperidine derivatives of the formula (I) and (II).

Hydrated, pharmaceutically acceptable acid addition salts of the compounds of formula (I) and (II) are those hydrates ranging from essentially 0.10 to 5 molecules of water per molecule of substrate salt of formula (I) or (II).

As used herein, the term "azeotropic mixture" refers to a liquid mixture of two or more substances which behaves like a single substance in that the vapor produced by partial evaporation of liquid has the same composition as the liquid. The constant boiling mixture exhibits either a maximum or minimum boiling point as compared with that of other mixtures of the same substance.

As used herein, the term "azeotropic distillation" refers to a type of distillation in which a substance is added to the mixture to be separated in order to form an azeotropic mixture with one or more of the constituents of the original mixture. The azeotrope or azeotropes thus formed will have boiling points different from the boiling points of the original mixture. As used herein, the term "azeotropic distillation" also refers to co-distillation.

As used herein, the term "water-minimizing recrystallization" refers to a recrystallization wherein the ratio of anhydrous solvent to substrate hydrate is such that the percentage of water present is minimized, thereby inducing precipitation of the anhydrous form of the substrate.

As used herein, the term "aqueous recrystallization" refers to those processes wherein either 1) a solid material is dissolved in a volume of water or a water/organic solvent mixture sufficient to cause dissolution and the solid material recovered by evaporation of the solvent; 2) a solid material is treated with a minimal amount of water or a water/organic solvent mixture which is not sufficient to cause dissolution, heated to obtain dissolution and cooled to induce crystallization or 3) a solid material is dissolved in a volume of water or a water/organic solvent mixture sufficient to cause dissolution and then the solvent is partially evaporated to form a saturated solution which induces crystallization.

As used herein, the term "crystal digestion" refers to that process wherein a solid material is treated with a minimal amount of water or water/organic solvent mixture which is not sufficient to cause dissolution and either heating or stirring at ambient temperature until the desired transformation has taken place.

As used herein, the term "antisolvent" refers to a poor solvent for the substance in question which when added to a solution of the substance, causes the substance to precipitate.

As used herein, the term "suitable temperature" refers to that temperature which is sufficient to cause dissolution and to permit the precipitation of the desired substance either upon addition of an antisolvent or upon removal of the co-solvent by azeotropic distillation.

The anhydrous, pharmaceutically acceptable acid addition salts of piperidine derivatives of the formula (I) and (II) may be prepared from the corresponding hydrated, pharmaceutically acceptable acid addition salts of piperidine derivatives of the formula (I) and (II) by subjecting the corresponding hydrated, pharmaceutically acceptable acid addition salts of piperidine derivatives of the formula (I) and (II) to an azeotropic distillation.

For example, the appropriate hydrated, pharmaceutically acceptable acid addition salt of piperidine derivatives of the formula (I) and (II) is first dissolved in a volume of a suitable solvent or solvent mixture which is sufficient to cause dissolution. Examples of such solvents are water, $C_1$–$C_5$ alkanols such as methanol, ethanol and the like; ketone solvents such as acetone, methyl ethyl ketone and the like; aliphatic ester solvents such as ethyl acetate, methyl acetate, methyl formate, ethyl formate, isopropyl acetate and the like and aqueous mixtures of these solvents, such as acetone/water, methyl ethyl ketone/water, water/acetone and water/acetone/ethyl acetate. An additional volume of the same solvent used to effect dissolution or second suitable anhydrous antisolvent is then added to this solution, which is then heated to a boiling point which is suitable to azeotropically remove water and other low boiling components. Suitable anhydrous antisolvents for use in the azeotropic distillation are, for example, ketone solvents such as acetone, methyl ethyl ketone and the like; aliphatic ester solvents such as ethyl acetate, methyl acetate, methyl formate, ethyl formate, isopropyl acetate and the like; $C_5$–$C_8$ aliphatic solvents such as pentane, hexane and the like; aliphatic nitriles, such as acetonitrile and mixtures of these solvents such as acetone/ ethyl acetate and the like. The azeotropic mixture of water and solvent is removed by distillation until the temperature changes, indicating that the azeotropic mixture is completely removed. The reaction mixture is cooled and the corresponding anhydrous, pharmaceutically acceptable acid addition salts of piperidine derivatives of the formula (I) and (II) is recovered from the reaction zone by, for example filtration.

In addition, the anhydrous, pharmaceutically acceptable acid addition salts of piperidine derivatives of the formula (I) and (II) may be prepared from the corresponding hydrated, pharmaceutically acceptable acid addition salts of piperidine derivatives of the formula (I) and (II) by subjecting the corresponding hydrated, pharmaceutically acceptable acid addition salts of piperidine derivatives of the formula (I) and (II) to a water-minimizing recrystallization.

For example, the appropriate hydrated, pharmaceutically acceptable acid addition salt of piperidine derivatives of the formula (I) and (II) is dissolved in a volume of a suitable anhydrous solvent or solvent mixture which is sufficient to cause dissolution and heated to reflux. Examples of such solvents are water, $C_1$–$C_5$ alkanols such as methanol, ethanol and the like; ketone solvents such as acetone, methyl ethyl ketone and the like; aliphatic ester solvents such as ethyl acetate, methyl acetate, methyl formate, ethyl formate, isopropyl acetate and the like and aqueous mixtures of these solvents, such as acetone/water, methyl ethyl ketone/water, water/acetone and water/acetone/ethyl acetate. An additional volume of the same solvent used to effect dissolution or second suitable anhydrous antisolvent is then added in a quantity sufficient to initiate precipitation of the anhydrous, pharmaceutically acceptable acid addition salt of piperidine derivatives of the formula (I) and (II). Suitable anhydrous antisolvents are, for example, ketone solvents such as acetone, methyl ethyl ketone and the like; aliphatic ester solvents such as ethyl acetate, methyl acetate, methyl formate, ethyl formate, isopropyl acetate and the like; mixtures of ketone solvents and aliphatic ester solvents such as acetone/ethyl acetate and the like; $C_5$–$C_8$ aliphatic solvents such as pentane, hexane and the like; aliphatic nitriles, such as acetonitrile and mixtures of these solvents such as acetone/ethyl acetate and the like as well as mixtures of water and ketone solvents such as acetone/water and the like; and mixtures of water, ketone solvents and aliphatic ester solvents such as acetone/water/ethyl acetate. The reaction mixture is cooled and the corresponding anhydrous, pharmaceutically acceptable acid addition salt of piperidine derivatives of the formula (I) and (II) is recovered from the reaction zone by, for example filtration.

Polymorphic forms of anhydrous 4-[4-[4-(Hydroxydiphenylmethyl)-1-piperidinyl]-1-hydroxybutyl]-α,α-dimethylbenzeneacetic acid hydrochloride (Forms I and III) may be prepared by a variety of methods as detailed below.

Form III to Form I

For example, anhydrous 4-[4-[4-(Hydroxydiphenylmethyl)-1-piperidinyl]-1-hydroxybutyl]-α,α-dimethylbenzeneacetic acid hydrochloride (Form I) may be prepared from anhydrous 4-[4-[4-(Hydroxydiphenylmethyl)-1-piperidinyl]-1-hydroxybutyl]-α,α-dimethylbenzeneacetic acid hydrochloride (Form III), by subjecting the anhydrous 4-[4-[4-(Hydroxydiphenylmethyl)-1-piperidinyl]-1-hydroxybutyl]-α,α-dimethylbenzeneacetic acid hydrochloride (Form III) to a crystal digestion as described above.

Form II to Form III

In addition, anhydrous 4-[4-[4-(Hydroxydiphenylmethyl)-1-piperidinyl]-1-hydroxybutyl]-α,α-dimethylbenzeneacetic acid hydrochloride (Form III) may be prepared from hydrated 4-[4-[4-(Hydroxydiphenylmethyl)-1-piperidinyl]-1-hydroxybutyl]-α,α-dimethylbenzeneacetic acid hydrochloride (Form II), by subjecting the hydrated 4-[4-[4-(Hydroxydiphenylmethyl)-1-piperidinyl]-1-hydroxybutyl]-α,α-dimethylbenzeneacetic acid hydrochloride (Form II) to water-minimizing recrystallization as described above.

Form II to Form I

In addition, anhydrous 4-[4-[4-(Hydroxydiphenylmethyl)-1-piperidinyl]-1-hydroxybutyl]-α,α-dimethylbenzeneacetic acid hydrochloride (Form I) may be prepared from hydrated 4-[4-[4-(Hydroxydiphenylmethyl)-1-piperidinyl]-1-hydroxybutyl]-α,α-dimethylbenzeneacetic acid hydrochloride (Form II), by subjecting the hydrated 4-[4-[4-(Hydroxydiphenylmethyl)-1-piperidinyl]-1-hydroxybutyl]-α,α-dimethylbenzeneacetic acid hydrochloride (Form II) to water-minimizing recrystallization as described above or by subjecting the hydrated 4-[4-[4-(Hydroxydiphenylmethyl)-1-piperidinyl]-1-hydroxybutyl]-α,α-dimethylbenzeneacetic acid hydrochloride (Form II) to an azeotropic distillation.

Form IV to Form I

In addition, anhydrous 4-[4-[4-(Hydroxydiphenylmethyl)-1-piperidinyl]-1-hydroxybutyl]-α,α-dimethylbenzeneacetic acid hydrochloride (Form I) may be prepared from hydrated 4-[4-[4-(Hydroxydiphenylmethyl)-1-piperidinyl]-1-hydroxybutyl]-α,α-dimethylbenzeneacetic acid hydrochloride (Form IV), by subjecting the hydrated 4-[4-[4-(Hydroxydiphenylmethyl)-1-piperidinyl]-1-hydroxybutyl]-α,α-dimethylbenzeneacetic acid hydrochloride (Form IV) to water-minimizing recrystallization or to an azeotropic distillation as described above.

The hydrated, pharmaceutically acceptable acid addition salts of piperidine derivatives of the formula (I) may be prepared from the corresponding compound of the formula (II) wherein $R_3$ is —COOalkyl by subjecting the corresponding compound of the formula (II) wherein $R_3$ is —COOalkyl to a reduction using an appropriate reducing agent, such as sodium borohyride, potassium borohydride, sodium cyanoborohydride, or tetramethylammonium borohydride in a suitable solvent, such as, methanol, ethanol, isopropyl alcohol or n-butanol, aqeuous mixtures thereof or basic solutions thereof, at temperatures ranging from about 0° C. to the reflux temperature of the solvent, and the reaction time varies from about ½ hour to 8 hours. After quenching and acidifying with an suitable acid, such as hydrochloric acid, the hydrated, pharmaceutically acceptable acid addition salts of piperidine derivatives of the formula (I) are recovered from the reaction zone by crystallization and filtration.

In addition, the hydrated, pharmaceutically acceptable acid addition salts of piperidine derivatives of the formula (I) and (II) may be prepared from the corresponding anhydrous, pharmaceutically acceptable acid addition salts of the formula (I) and (II) by subjecting the corresponding anhydrous, pharmaceutically acceptable acid addition salts of formula (I) and (II) to an aqueous recrystallization.

For example, the appropriate anhydrous, pharmaceutically acceptable acid addition salt of piperidine derivatives of the formula (I) and (II) is treated with a minimal volume of water or suitable water/organic solvent mixture which is insufficient to cause dissolution and heated to reflux. The reaction mixture is cooled and the corresponding hydrated, pharmaceutically acceptable acid addition salt of piperidine derivatives of the formula (I) and (II) is recovered from the reaction zone by, for example filtration. Alternatively, the appropriate anhydrous, pharmaceutically acceptable acid addition salt of piperidine derivatives of the formula (I) and (II) is treated with a volume of water or a suitable water/organic solvent mixture which is sufficient to cause dissolution and the water or water/organic solvent is partially or completely evaporated to a volume which induces crystallization of the hydrated, pharmaceutically acceptable acid addition salts of piperidine derivatives of the formula (I) and (II). Suitable solvents for use in the above recrystallization are water, acetone/water, ethanol/water, methyl ethyl ketone/aqueous methanol, methyl ethyl ketone/water and the like.

The pseudomorphic forms of hydrated 4-[4-[4-(Hydroxydiphenylmethyl)-1-piperidinyl]-1-hydroxybutyl]-α,α-dimethylbenzeneacetic acid hydrochloride (Forms II and IV) may be prepared by a variety of methods as detailed below.

Ethyl Ester/Ketone to Form II

Hydrated 4-[4-[4-(Hydroxydiphenylmethyl)-1-piperidinyl]-1-hydroxybutyl]-α,α-dimethylbenzeneacetic acid hydrochloride (Form IV) may be prepared from ethyl 4-[4-[4-(hydroxydiphenylmethyl)-1-piperidinyl]-1-oxobutyl]-α,α-dimethylbenzeneacetate, hydrochloride or free base as described above for the general preparation of the hydrated, pharmaceutically acceptable acid addition salts of piperidine derivatives of the formula (I) from the corresponding compound of the formula (II) wherein $R_3$ is —COOalkyl, but rapidly adding water over a period of time ranging from 1 minute to 45 minutes at a temperature range of about −20° C. to 50° C. to precipitate the hydrated 4-[4-[4-(Hydroxydiphenylmethyl)-1-piperidinyl]-1-hydroxybutyl]-α,α-dimethylbenzeneacetic acid hydrochloride (Form II).

Ethyl Ester/Ketone to Form IV

Hydrated 4-[4-[4-(Hydroxydiphenylmethyl)-1-piperidinyl]-1-hydroxybutyl]-α,α-dimethylbenzeneacetic acid hydrochloride (Form IV) may be prepared from ethyl 4-[4-[4-(hydroxydiphenylmethyl)-1-piperidinyl]-1-oxobutyl]-α,α-dimethylbenzeneacetate, hydrochloride or free base as described above for the general preparation of the hydrated, pharmaceutically acceptable acid addition salts of piperidine derivatives of the formula (I) from the corresponding compound of the formula (II) wherein $R_3$ is —COOalkyl, but slowly adding water over a period of time ranging from about 30 minutes to 24 hours and at a temperature range of about 0° C. to 50° C., optionally with seeding, to precipitate the hydrated 4-[4-[4-(Hydroxydiphenylmethyl)-1-piperidinyl]-1-hydroxybutyl]-α,α-dimethylbenzeneacetic acid hydrochloride (Form IV).

Form I to Form II

Hydrated 4-[4-[4-(Hydroxydiphenylmethyl)-1-piperidinyl]-1-hydroxybutyl]-α,α-dimethylbenzeneacetic acid hydrochloride (Form II) may be prepared from anhydrous 4-[4-[4-(Hydroxydiphenylmethyl)-1-piperidinyl]-1-hydroxybutyl]-α,α-dimethylbenzeneacetic acid hydrochloride (Form I) by subjecting hydrated 4-[4-[4-(Hydroxydiphenylmethyl)-1-piperidinyl]-1-hydroxybutyl]-α,α-dimethylbenzeneacetic acid hydrochloride (Form II) to an aqueous recrystallization as defined above.

Starting materials for use in the present invention are readily available to one of ordinary skill in the art. For example, ethyl 4-[4-[4-(Hydroxydiphenylmethyl)-1-piperidinyl]-1-oxobutyl]-α,α-dimethylbenzeneacetate, hydrochloride is described in U.S. Pat. No. 4,254,129, Mar. 3, 1981.

The following examples present typical processes for preparing the anhydrous and hydrated, pharmaceutically acceptable acid addition salts of piperidine derivatives of the formula (I) and (II), polymorphs and pseudomorphs therof. These examples are understood to be illustrative only and are not intended to limit the scope of the present invention in any way. As used herein, the following terms have the indicated meanings: "g" refers to grams; "mol" refers to mole; "mmol" refers to millimoles; "mL" refers to milliliters; "bp" refers to boiling point; "mp" refers to melting point; "° C.", refers to degrees Celsius; "mm Hg" refers to millimeters of mercury; "μL" refers to microliters; "μg" refers to micrograms; and "μM" refers to micromolar.

Differential Scanning Calorimetry analysis were performed using a TA 2910 DSC with open aluminum pans. The samples were heated to 240° C. at 5° C./minute with a 50 mL/minute nitrogen purge.

X-Ray Powder Diffraction analyses were performed as follows:

The samples were loaded into a quartz (zero scatter) sample holder for the XR?D pattern measurement. The XRPD patterns were measured using a powder diffractometer equipped with a Co X-ray tube source, primary beam monochromator, and position sensitive detector (PSD). The incident beam was collimated using a 1° divergence slit. The active area on the PSD subtended approximately 5° 2Θ). The source was operated at 35 kV and 30 mA and the sample was illuminated with Co Kα$_1$ radiation. XRPD data were collected from 5 to 55° 2Θ at a rate of 0.25° 2Θ/minute and a step width of 0.02° 2Θ. The XRPD patterns were measured without the addition of an internal calibrant.

Peak positions and intensities for the most prominent features were measured using a double-derivative peak picking method. X-ray peaks with $I/I_o$ greater than 20% were reported. The cutoff was chosen arbitrarily. The intensities are rounded to the nearest 5%. Certain peaks appear sensitive to preferred orientation that is caused by changes in crystallite morphology. This results in large changes in the $I/I_o$ value.

EXAMPLE 1

Preparation of Form II 4-[4-[4-(Hydroxydiphenylmethyl)-1-piperidinyl]-1-hydroxybutyl]-α,α-dimethylbenzeneacetic acid hydrochloride Method A Mix ethyl 4-[4-[4-(hydroxydiphenylmethyl)-1-piperidinyl]-1-oxobutyl]-α,α-dimethylbenzeneacetate, hydrochloride (101.92 g, 0.1807 mol) and methanol (510 mL) and stir. Rapidly add 50% sodium hydroxide (72.27 g, 0.903 mol) and wash in with water (61 mL). Heat to reflux for 2 hours, allow to cool to 35° C. and treat with sodium borohydride (3.42 g, 0.0903 mol). Add water (100 mL) and maintain at 35° C. for 10 hours. Add 37% hydrochloric acid (53.0 g) to adjust pH to 11.5. Add acetone (26.5 mL) and water (102 mL). Hold at 35° C. for 2 hours and adjust to pH 2.5 with 37% hydrochloric acid (44.69 g). Dilute with water (408 mL), cool to −15° C., stir for 1.5 hours and collect the precipitate by vacuum filtration. Wash the filtercake with deionized water (3×100 mL) and vacuum dry to give 4-[4-[4-(hydroxydiphenylmethyl)-1-piperidinyl]-1-hydroxybutyl]-α,α-dimethylbenzeneacetic acid hydrochloride hydrate (97.10 g).

Method B

Place ethyl 4-[4-[4-(hydroxydiphenylmethyl)-1-piperidinyl]-1-oxobutyl]-α,α-dimethylbenzeneacetate, hydrochloride (60.01 g, 0.106 mol) in a 1-L three necked round-bottom flask and fit the flask with a mechanical stirrer, a Claisen head, a thermometer and a reflux condenser with a nitrogen bubbler on top. Add methanol (300 mL) and turn the stirrer on. Dilute the slurry with water (60 mL) and heat to 52–54° C. over 15–20 minutes. Hold at 52° C. for 2 hours and then add 50% sodium hydroxide (42.54 g, 0.532 mol). Heat at 73° C. for approximately 1 hour, 45 minutes, cool to less than 35° C. using a water bath and then add sodium borohydride (2.02 g, 0.0534 mol). Stir overnight at 35° C., treat with acetone (15.5 mL) and stir for 2 hours at 35° C. Acidify the mixture to a pH of 1.85 with 28% hydrochloric acid (75.72 g), dilute with water (282 mL), stir for about 30 minutes and cool over about 2 hours to −15° C. Filter the solids off and wash with water (2×75 mL) and ethyl acetate (2×75 mL). Vacuum dry the solid and allow to stand for 2 days to give 4-[4-[4-(hydroxydiphenylmethyl)-1-piperidinyl]-1-hydroxybutyl]-α,α-dimethylbenzeneacetic acid hydrochloride hydrate (Form II) (57.97 g, 91.5%) as a fine powder.

Method C

Place ethyl 4-[4-[4-(hydroxydiphenylmethyl)-1-piperidinyl]-1-oxobutyl]-α,α-dimethylbenzeneacetate (56.12 g, 0.1064 mol) in a 1-L three necked round-bottom flask and fit the flask with a mechanical stirrer, a Claisen head, a thermometer and a reflux condenser with a nitrogen bubbler on top. Add methanol (300 mL) and turn the stirrer on. Dilute the slurry with water (60 mL) and heat to reflux using a heating mantle controlled by a Therm-O-Watch. When the mixture reaches about 35° C., treat with 50% sodium hydroxide (34.05 g, 0.4256 mol) and rinse in with water (42 mL). Stir at reflux for 2 hours, 15 minutes, cool over 1 hour to 35° C. and then treat with sodium borohydride (2.02 g, 0.0534 mol). Stir for 7.5 hours and allow to stand at room temperature without stirring for 1.75 days. Warm the mixture to 35° C. and quench with acetone (15.5 mL, 0.21 mol) and stir for 2 hours. Add water (60 mL) and adjust the pH to 2.5 with 32% hydrochloric acid (65.22 g). Cool to 40° C. and rinse the pH probe with water (25 mL). Add water over about 30 minutes (192 mL), hold the temperature at 33° C. for 10 minutes and add a few seed crystals. Cool the slurry to −12° C. over about 45. minutes and isolate the solid by filtration (586.2 g). Wash with water (2×100 mL) and then with ethyl acetate (100 mL, prechilled to about −10° C.). Vacuum dry overnight (1 mmHg, 50° C.) to give 4-[4-[4-(hydroxydiphenylmethyl)-1-piperidinyl]-1-hydroxybutyl]-α,α-dimethylbenzeneacetic acid hydrochloride hydrate (Form II) (58.86 g, 98%) as a white solid.

EXAMPLE 2

Preparation of Form IV 4-[4-[4-(hydroxydiphenylmethyl)-1-piperidinyl]-1-hydroxybutyl]-α,α-dimethylbenzeneacetic acid hydrochloride (Form IV)

Place ethyl 4-[4-[4-(hydroxydiphenylmethyl)-1-piperidinyl]-1-oxobutyl]-α,α-dimethylbenzeneacetate (56.12 g, 0.1064 mol) in a 1-L three necked round-bottom flask and fit the flask with a mechanical stirrer, a Claisen head, a thermometer and a reflux condenser with a nitrogen bubbler on top. Add methanol (300 mL) and turn the stirrer on. Dilute the slurry with water (60 mL) and heat to reflux using a heating mantle controlled by a Therm-O-Watch. When the mixture reaches about 35° C., treat with 50% sodium hydroxide (34.05 g, 0.4256 mol) and rinse in with water (42 mL). Stir at reflux for 2 hours, 15 minutes, cool over 1 hour to 35° C. and then treat with sodium borohydride (2.02 g, 0.0534 mol). Stir for 7.5 hours and allow to stand at room temperature without stirring for 1.75 days. Warm the mixture to 35° C. and quench with acetone (15.5 mL, 0.21 mol) and stir for 2 hours. Add water (60 mL) and adjust the pH to 2.5 with 32% hydrochloric acid (65.22 g). Cool to 40° C. and rinse the pH probe with water (25 mL). Hold the temperature at 33° C. for 10 minutes, add a few seed crystals and add water over about 4 hours (192 mL) at 35° C. Cool the slurry to −12° C. over about 45 minutes and isolate the solid by filtration (586.2 g). Wash with water (2×100 mL) and then with ethyl acetate (100 mL, prechilled to about −10° C.). Vacuum dry overnight (1 mmHg, 50° C.) to give 4-[4-[4-(hydroxydiphenylmethyl)-1-piperidinyl]-1-hydroxybutyl]-α,α-dimethylbenzeneacetic acid hydrochloride hydrate (Form IV); mp 115–116° C. (dec).

XRPD: Table 5

TABLE 5

| D-Space, Angstroms | Intensity, $I/I_o$, % |
| --- | --- |
| 10.38 | 60 |
| 6.97 | 45 |
| 6.41 | 50 |
| 5.55 | 30 |
| 5.32 | 100 |
| 5.23 | 55 |
| 5.11 | 35 |
| 4.98 | 25 |
| 4.64 | 30 |
| 4.32 | 35 |
| 4.28 | 75 |
| 4.12 | 50 |
| 4.02 | 45 |
| 3.83 | 60 |
| 3.65 | 20 |
| 3.51 | 55 |
| 3.46 | 25 |
| 2.83 | 20 |

EXAMPLE 3

Conversion of Form II to Form I 4-[4-[4-(hydroxydiphenylmethyl)-1-piperidinyl]-1-hydroxybutyl]-, -dimethylbenzeneacetic acid hydrochloride (Form I)

Treat 4-[4-[4-(hydroxydiphenylmethyl)-1-piperidinyl]-1-hydroxybutyl]-, -dimethylbenzeneacetic acid hydrochloride hydrate (Form II) (20.0 g, 0.0355 mol) with deionized water (2 g) and add acetone (60 mL) in small portions over several minutes with stirring. Filter through filter aid and wash the filter cake with acetone (30 mL). Wash the filtercake with acetone (22 mL), reflux filtrate and then slowly add ethyl acetate (32 mL over 15 minutes) keeping the mixture at reflux. Reflux for 10 minutes, then slowly add additional ethyl acetate (23 mL over 10 minutes) and reflux for an additional 15 minutes. Add additional ethyl acetate (60 mL over 5–10 minutes) and continue refluxing for 15 minutes. Cool to approximately 8° C. in an ice bath, filter the solid and wash with ethyl acetate (85 mL). Vacuum dry at 55° C. for 1.5 hours to give the title compound (18.16 g, 95%).

EXAMPLE 4

Conversion of Form II to Form I 4-[4-[4-(Hydroxy-diphenylmethyl)-1-piperidinyl]-1-hydroxybutyl]-α, α-dimethylbenzeneacetic acid hydrochloride Method A:
Treat 4-[4-[4-(hydroxydiphenylmethyl)-1-piperidinyl]-1-hydroxybutyl]-α,α-dimethylbenzeneacetic acid hydrochloride hydrate (Form II) (5.00 g, 0.0083 mol) with methylethyl ketone (130 mL). Slowly add water (0.4 mL), filter through filter aid and wash the filter cake with methylethyl ketone (20 mL). Heat to reflux and distill off 75 mL of solvent, cool to −15° C. and collect by vacuum filtration. Wash with methylethyl ketone (2×10 mL) and vacuum dry at 60° C. to give the title compound (4.33 g, 97%); mp 196–198° C.

Method B:
Treat 4-[4-[4-(hydroxydiphenylmethyl)-1-piperidinyl]-1-hydroxybutyl]-α,α-dimethylbenzeneacetic acid hydrochloride hydrate (Form II) (1.4 g) with acetone (60 mL) and heat to reflux. Reduce the volume to approximately 35 mL to remove all water which boils off as an azeotrope (88/12: acetone/water). Cool the solution and collect the title compound as a crystalline solid.

Method C:
Mix 4-[4-[4-(hydroxydiphenylmethyl)-1-piperidinyl]-1-hydroxybutyl]-α,α-dimethylbenzeneacetic acid hydrochloride hydrate (Form II) (53.88 g, 0.100 mol) and add water (4.79 g) and methyl ethyl ketone (240 mL). Stir until the solid is slurried up and add additional methyl ethyl ketone (1L). Stir for 0.5 hours, filter through a pad of filter aid, wash the filtercake with methyl ethyl ketone (100 mL) and transfer the filtrate and wash to a 2L, 3-necked flask fitted with a thermometer, mechanical stirrer and distillation head. Distill off a total of 72 mL of methyl ethyl ketone, cool and stir over 1 hour to 40° C. Cool to −15° C. and hold for 10 minutes. Collect the solid by vacuum filtration and wash the filtercake with methyl ethyl ketone (2×65 mL) and vacuum dry at 55° C. overnight to give the title compound (52.76 g, 97.9%); mp 197.5–200° C.

Method D:
Treat 4-[4-[4-(hydroxydiphenylmethyl)-1-piperidinyl]-1-hydroxybutyl]- , -dimethylbenzeneacetic acid hydrochloride hydrate (Form II) (40.0 g, 0.0696 mol, assayed at 93.6% purity, having 0.89 g water present and 35.1 g, 0.0575 mol, assayed at 88.0% purity, having 2.47 g water present) with water (8.30 g; the amount calculated to bring the weight of water present to 17% of the anhydrous weight of 4-[4-[4-(hydroxydiphenylmethyl)-1-piperidinyl]-1-hydroxybutyl]- , -dimethylbenzeneacetic acid hydrochloride hydrate, taking into account the water in the hydrated salt). Add methyl ethyl ketone (approximately 500 mL) and stir until most of the solids dissolve. Add additional methyl ethyl ketone (700 mL) in portions over approximately 10 minutes and continue stirring for ½ hour. Filter through a thin pad of filter aid, wash the filtercake and flask with additional methyl ethyl ketone (100 mL) and transfer to a boiling flask fitted with a thermometer, mechanical stirrer, heating mantle, a 12-plate Oldershaw (vacuum-jacketed) distillation column and a distillation head with the capability of regulating the reflux ratio in a rough fashion, washing in with additional methyl ethyl ketone (100 mL). Distill off 450 mL of solvent, cool to −15° C. and filter the solid. Wash with methyl ethyl ketone (2×100 mL) and dry to give the title compound (68.3 g, 99.9%); mp 197–199° C.

Method E:
Bring methyl ethyl ketone (4 mL) to a boil and add 4-[4-[4-(hydroxydiphenylmethyl)-1-piperidinyl]-1-hydroxybutyl]- , -dimethylbenzeneacetic acid hydrochloride (500 mg). Decant the top layer and add methyl ethyl ketone (3 mL) to the aqeuous layer. Boil the solution until the temperature reached 79° C., reduce the volume by 25%, remove from heat and cover with aluminum foil. Allow the solution to cool, filter the resulting crystals and air dry to give the title compound.

EXAMPLE 5

Conversion of Form I to Form II 4-[4-[4-(Hydroxy-diphenylmethyl)-1-piperidinyl]-1-hydroxybutyl]- , -dimethylbenzeneacetic acid hydrochloride hydrate Method A
Treat 4-[4-[4-(hydroxydiphenylmethyl)-1-piperidinyl]-1-hydroxybutyl]- , -dimethylbenzeneacetic acid hydrochloride (Form I) (2.0 g) with ethanol (4 mL) and deionized water (20 mL). Heat at 80° C. until a solution is formed and then stir at room temperature for 23 hours. Filter the resulting slurry, wash with water (2×10 mL) and dry under vacuum at 35° C. overnight to give the title compound (1.88 g); mp 100–105° C.

XRPD: Table 6

TABLE 6

| D-Space, Angstroms | Intensity, $I/I_o$, % |
|---|---|
| 11.41 | 20 |
| 7.98 | 20 |
| 7.83 | 45 |
| 6.58 | 45 |
| 6.42 | 60 |
| 5.66 | 20 |
| 5.52 | 45 |
| 5.39 | 30 |
| 5.23 | 65 |
| 5.14 | 45 |
| 4.86 | 65 |
| 4.72 | 100 |
| 4.45 | 65 |
| 4.40 | 45 |
| 4.32 | 45 |
| 4.18 | 45 |
| 4.06 | 65 |
| 4.02 | 55 |
| 3.85 | 25 |
| 3.79 | 75 |
| 3.74 | 95 |
| 3.61 | 80 |
| 3.56 | 25 |
| 3.47 | 65 |
| 3.41 | 20 |
| 2.74 | 20 |

Method B
Mix water (35.5 mL), methanol (26.3 mL) and sodium chloride (2.59 g). Add 4-[4-[4-(hydroxydiphenylmethyl)-1-piperidinyl]-1-hydroxybutyl]-α,α-dimethylbenzeneacetic acid hydrochloride (Form I) (4.77 g). Heat to reflux on a steam bath until dissolution and cool to −10° C. Filter the resulting solid, wash with water (2×25 mL) and vacuum dry overnight to give the title compound (4.80 g).

EXAMPLE 6

Conversion of Form II into Form III 4-[4-[4-(Hydroxydiphenylmethyl)-1-piperidinyl]-1-hydroxybutyl]-α,α-dimethylbenzeneacetic acid hydrochloride (Form III)

Place 4-[4-[4-(Hydroxydiphenylmethyl)-1-piperidinyl]-1-hydroxybutyl]-α,α-dimethylbenzeneacetic acid hydrochloride hydrate (Form II) (55.56 g, 0.0929 mol having 10% water) in a pressure bottle along with water (2.96 g) and acetone (38.1 g). Seal the bottle tightly and heat to approximately 80° C. Cool to about 50° C., filter through filter aid in a coarse sintered glass funnel and dilute with acetone (90 g). Transfer to a 1L flask fitted with a mechanical stirrer, thermometer and a reflux condenser. Heat the mixture to reflux and allow to cool and stir over the weekend. Cool to −15° C. and filter on a coarse sintered glass funnel, wash with ethyl acetate (2×50 mL) and vacuum dry at 50° C.

Place a majority of the solid obtained (45.24 g) in a 500 mL three necked flask fitted with a mechanical stirrer, thermometer and a reflux condenser. Add acetone (240 mL) and water (4.82 g) and reflux the mixture overnight. Allow the slurry to cool to 35° C. and place in an ice water bath and cool to less then 5° C. Filter the solid off on a coarse sintered glass funnel, wash with ethyl acetate (50 mL) and vacuum dry at 50 C for several hours to give the title compound as a white crystalline powder (43.83 g, 97%); mp 166.5–170.5° C.

XRPD: Table 7

TABLE 7

| D-Space, Angstroms | Intensity, I/I$_o$, % |
|---|---|
| 8.95 | 95 |
| 4.99 | 20 |
| 4.88 | 100 |
| 4.75 | 35 |
| 4.57 | 25 |
| 4.47 | 25 |
| 4.46 | 20 |
| 3.67 | 20 |
| 3.65 | 25 |

EXAMPLE 7

Conversion of Form III into Form I 4-[4-[4-(Hydroxydiphenylmethyl)-1-piperidinyl]-1-hydroxybutyl]-α,α-dimethylbenzeneacetic acid hydrochloride (Form I)

Place 4-[4-[4-(Hydroxydiphenylmethyl)-1-piperidinyl]-1-hydroxybutyl]-α,α-dimethylbenzeneacetic acid hydrochloride (Form III) (40.0 g as an ethyl acetate wetcake-27.9 g dry basis) in a 1L three necked flask fitted with a mechanical stirrer, thermometer and a reflux condenser. Add acetone (240 mL) and heat the mixture to reflux for about 20 hours. Cool the slurry to −15° C. and isolate the solids by filtration on a coarse sintered glass frit funnel. Wash with ethyl acetate (50 mL) and vacuum dry overnight to give the title compound (26.1 g, 93.7%); mp 197.5–199.5° C.

XRPD: Table 8

TABLE 8

| D-Space, Angstroms | Intensity, I/I$_o$, % |
|---|---|
| 11.75 | 35 |
| 7.23 | 35 |
| 6.24 | 60 |
| 5.89 | 40 |
| 5.02 | 20 |
| 4.94 | 30 |
| 4.83 | 100 |
| 4.44 | 30 |
| 3.93 | 75 |
| 3.83 | 20 |
| 3.77 | 85 |
| 3.71 | 25 |
| 3.62 | 30 |
| 3.32 | 25 |
| 3.31 | 20 |

EXAMPLE 8

Conversion of Form IV into Form I 4-[4-[4-(Hydroxydiphenylmethyl)-1-piperidinyl]-1-hydroxybutyl]-α,α-dimethylbenzeneacetic acid hydrochloride (Form I)

Place 4-[4-[4-(hydroxydiphenylmethyl)-1-piperidinyl]-1-hydroxybutyl]-α,α-dimethylbenzeneacetic acid hydrochloride hydrate (Form IV) (54.35 g, 0.0970 mol, having 4% water present) in a pressure bottle along with water (4.16 g) and acetone (38.1 g). Seal the bottle tightly and heat to approximately 80° C. Cool to less then 60° C., filter through filter aid in a coarse sintered glass funnel and rinse the filter cake with acetone (32.4 g). Place acetone (215 g) in a 1L three necked flask fitted with a mechanical stirrer, thermometer, a reflux condenser and containing a small amount of Form I crystals and heat to reflux. Add a portion of the acetone/water solution of 4-[4-[4-(hydroxydiphenylmethyl)-1-piperidinyl]-1-hydroxybutyl]-α,α-dimethylbenzeneacetic acid hydrochloride hydrate (Form IV) (47.65 g) to the refluxing acetone over about 10 minutes. Slowly add ethyl acetate (157.5 g) over 45 minutes then add the remaining portion of the acetone/water solution of 4-[4-[4-(hydroxydiphenylmethyl)-1-piperidinyl]-1-hydroxybutyl]-α,α-dimethylbenzeneacetic acid hydrochloride hydrate (Form IV), rinsed in with about 20 mL of acetone. Add additional ethyl acetate (157.5 g) over 45 minutes to 1 hour, maintaining the slurry at reflux. Stir for 15 minutes, cool to −15° C. and vacuum filter the white solid on a 350 mL coarse sintered glass funnel. Wash the solids with ethyl acetate (2×50 mL) and vacuum dry overnight to give the title compound (50.36 g, 97%); mp 198–199.5° C.

XRPD: Table 9

TABLE 9

| D-Space, Angstroms | Intensity, I/I$_o$, % |
|---|---|
| 14.89 | 20 |
| 11.85 | 20 |
| 7.30 | 20 |
| 6.28 | 70 |
| 5.91 | 25 |
| 5.55 | 20 |
| 5.05 | 25 |

TABLE 9-continued

| D-Space, Angstroms | Intensity, I/I₀, % |
|---|---|
| 4.96 | 55 |
| 4.85 | 100 |
| 4.57 | 45 |
| 4.45 | 55 |
| 3.94 | 45 |
| 3.89 | 20 |
| 3.84 | 20 |
| 3.78 | 60 |
| 3.72 | 35 |
| 3.63 | 20 |
| 3.07 | 20 |
| 3.04 | 20 |
| 2.45 | 20 |

The polymorphic and pseudomorphic 4-[4-[4-(hydroxydiphenylmethyl)-1-piperidinyl]-1-hydroxybutyl]-α,α-dimethylbenzeneacetic acid hydrochloride compounds of this invention are useful as antihistamines, antiallergy agents and bronchodilators and may be administered alone or with suitable pharmaceutical carriers, and can be in solid or liquid form such as, tablets, capsules, powders, solutions, suspensions or emulsions.

The polymorphic and pseudomorphic 4-[4-[4-(hydroxydiphenylmethyl)-1-piperidinyl]-1-hydroxybutyl]-α,α-dimethylbenzeneacetic acid hydrochloride compounds of this invention can be administered orally, parenterally, for example, subcutaneously, intravenously, intramuscularly, intraperitoneally, by intranasal instillation or by application to mucous membranes, such as, that of the nose, throat and bronchial tubes, for example, in an aerosol spray containing small particles of a compound of this invention in a spray or dry powder form.

The quantity of polymorphic or pseudomorphic 4-[4-[4-(hydroxydiphenylmethyl)-1-piperidinyl]-1-hydroxybutyl]-α,α-dimethylbenzeneacetic acid hydrochloride compound administered will vary depending on the patient and the mode of administration and can be any effective amount. The quantity of polymorphic or pseudomorphic 4-[4-[4-(hydroxydiphenylmethyl)-1-piperidinyl]-1-hydroxybutyl]-α,α-dimethylbenzeneacetic acid hydrochloride compound administered may vary over a wide range to provide in a unit dosage an effective amount of from about 0.01 to 20 mg/kg of body weight of the patient per day to achieve the desired effect. For example, the desired antihistamine, antiallergy and bronchodilator effects can be obtained by consumption of a unit dosage form such as a tablet containing 1 to 500 mg of a polymorphic or pseudomorphic 4-[4-[4-(hydroxydiphenylmethyl)-1-piperidinyl]-1-hydroxybutyl]-α,α-dimethylbenzeneacetic acid hydrochloride compound of this invention taken 1 to 4 times daily.

The solid unit dosage forms can be of the conventional type. Thus, the solid form can be a capsule which can be the ordinary gelatin type containing a polymorphic or pseudomorphic 4-[4-[4-(hydroxydiphenylmethyl)-1-piperidinyl]-1-hydroxybutyl]-α,α-dimethylbenzeneacetic acid hydrochloride compound of this invention and a carrier, for example, lubricants and inert fillers such as lactose, sucrose or cornstarch. In another embodiment the polymorphic or pseudomorphic 4-[4-[4-(hydroxydiphenylmethyl)-1-piperidinyl]-1-hydroxybutyl]-α,α-dimethylbenzeneacetic acid hydrochloride compound is tableted with conventional tablet bases such as lactose, sucrose or cornstarch or gelatin, disintegrating agents such as cornstarch, potato starch or alginic acid, and a lubricant such as stearic acid or magnesium stearate.

The polymorphic or pseudomorphic 4-[4-[4-(hydroxydiphenylmethyl)-1-piperidinyl]-1-hydroxybutyl]-α,α-dimethylbenzeneacetic acid hydrochloride compounds of this invention may also be administered in injectable dosages by solution or suspension of the compounds in a physiologically acceptable diluent with a pharmaceutical carrier which can be a sterile liquid such as water and oils, with or without the addition of a surfactant and other pharmaceutically acceptable adjuvants. Illustrative of oils there can be mentioned those of petroleum, animal, vegatable or synthetic origin, for example, peanut oil, soybean oil or mineral oil. In general, water, saline, aqueous dextrose and related sugar solutions and glycols such as propylene glycol or polyethylene glycol are preferred liquid carriers, particularly for injectable solutions.

For use as aerosols the compounds of this invention in solution or suspension may be packaged in a pressurized aerosol container together with suitable propellants, for example, hydrocarbon propellants such as, propane, butane or isobutane with the usual adjuvants as may be administered in a non-pressurized form such as in a nebulizer or atomizer.

The term patient as used herein is taken to mean warm blooded animals, birds, mammals, for example, humans, cats, dogs, horses, sheep, bovine cows, pigs, lambs, rats, mice and guinea pigs.

What is claimed is:

1. Form II hydrated 4-[4-[4-(Hydroxydiphenylmethyl)-1-piperidinyl]-1-hydroxybutyl]-α,α-dimethylbenzeneacetic acid hydrochloride.

* * * * *

UNITED STATES PATENT AND TRADEMARK OFFICE
CERTIFICATE OF CORRECTION

| | | |
|---|---|---|
| PATENT NO. | : 7,135,571 B2 | Page 1 of 1 |
| APPLICATION NO. | : 10/160883 | |
| DATED | : November 14, 2006 | |
| INVENTOR(S) | : Frederick J. McCarty | |

It is certified that error appears in the above-identified patent and that said Letters Patent is hereby corrected as shown below:

Title Page, Below Item (12) Delete "Henton et al." and insert --McCarty--.

On the Title page, Item (75) in the Inventors, lines 1-5 "Daniel R Henton, Midland, MI (US); Frederick J McCarty, Cincinnati, OH (US); Susan I Tripp, Lee's Summit, MO (US); Jill E DeWitt, Kansas City, MO (US)" should read --Frederick J McCarty, Cincinnati, OH (US)--.

Signed and Sealed this

Thirtieth Day of January, 2007

JON W. DUDAS
*Director of the United States Patent and Trademark Office*